United States Patent
Tachihata et al.

[11] Patent Number: 5,944,392
[45] Date of Patent: Aug. 31, 1999

[54] ROAD SURFACE CONDITION DETERMINING SYSTEM

[75] Inventors: Tetsuya Tachihata; Fumio Kageyama, both of Hiroshima, Japan

[73] Assignee: Mazda Motor Corporation, Hiroshima, Japan

[21] Appl. No.: 08/624,900

[22] Filed: Mar. 27, 1996

[30] Foreign Application Priority Data

Mar. 27, 1995 [JP] Japan .................................. 7-094288

[51] Int. Cl.$^6$ ...................................................... B60T 8/00
[52] U.S. Cl. ............................ 303/112; 303/141; 303/150
[58] Field of Search .................................. 303/112, 141, 303/142, 148, 149, 150, 140

[56] References Cited

U.S. PATENT DOCUMENTS

| | | | |
|---|---|---|---|
| 4,933,856 | 6/1990 | Leiber | 303/140 X |
| 5,077,672 | 12/1991 | Nobumoto et al. | 303/141 X |
| 5,135,290 | 8/1992 | Cao | 303/112 X |
| 5,211,452 | 5/1993 | Okazaki et al. | 303/150 |
| 5,320,422 | 6/1994 | Tsuyama et al. | 303/141 |
| 5,325,300 | 6/1994 | Tsuyama et al. | 303/141 X |
| 5,351,192 | 9/1994 | Tsuyama et al. | 303/150 X |
| 5,406,486 | 4/1995 | Kamio et al. | 303/150 X |
| 5,419,624 | 5/1995 | Adler et al. | 303/141 X |
| 5,421,644 | 6/1995 | Prescott et al. | 303/150 X |

FOREIGN PATENT DOCUMENTS

| | | |
|---|---|---|
| 60-99757 | 6/1985 | Japan . |
| 404135954 | 5/1992 | Japan ..................................... 303/142 |
| 4-328063 | 11/1992 | Japan . |

Primary Examiner—Robert J. Oberleitner
Assistant Examiner—Pamela J. Lipka
Attorney, Agent, or Firm—Morrison & Foerster LLP

[57] ABSTRACT

A road surface condition determining system for an automotive vehicle equipped with a traction control feature determines, while the traction control is being executed, a first road surface friction coefficient on the basis of a vehicle speed and longitudinal acceleration and a second road surface friction coefficient on the basis of driving torque applied to the driving wheels and selects, as an eventual road surface friction coefficient, either one of the first and second road surface friction coefficients which is larger than the other.

15 Claims, 5 Drawing Sheets

FIG. 4

|  | SMALL ← | | | LG | | → | | LARGE |
|---|---|---|---|---|---|---|---|---|
| SMALL ↑ Nv ↓ LARGE | 1.0 | 1.0 | 1.3 | 1.7 | | 5.0 | 5.0 | 5.0 |
| | 1.0 | 1.0 | 1.3 | 1.7 | | 5.0 | 5.0 | 5.0 |
| | 1.0 | 1.0 | 1.3 | 1.7 | | 5.0 | 5.0 | 5.0 |
| | 1.0 | 1.0 | 1.4 | 1.7 | | 5.0 | 5.0 | 5.0 |
| | 1.0 | 1.4 | 1.8 | 2.2 | | 5.0 | 5.0 | 5.0 |
| | 1.1 | 1.5 | 1.9 | 2.2 | | 5.0 | 5.0 | 5.0 |

FIG. 5

| LTG | | → | LARGE | |
|---|---|---|---|---|
| 1.0 | 2.0 | 3.0 | 4.0 | 4.0 |

FIG. 6

| Nv | → | LARGE |
|---|---|---|
| 1.0 | 2.5 | 4.0 |

ROAD SURFACE CONDITION DETERMINING SYSTEM

FIELD OF THE INVENTION

The invention relates to a road surface condition monitoring system which road surface conditions are monitored on the basis of estimation of the coefficient of friction of a road surface.

DESCRIPTION OF PRIOR ART

Traction control systems of the type which are able to prevent the loss of traction of driving wheels against the road surface during a vehicle start or acceleration are increasingly installed in automotive vehicles. The slip value utilized by these traction control systems, that is, the value at which the driving wheels lose traction in relation to the road surface, has been applied as a specific target slip value in feedback control of engine output torque. Such a traction control system estimates the frictional coefficient of road surface $\mu$ according to which the target slip value is adjusted and/or which can also be applied to antilock braking control.

One of the techniques of estimating the road surface friction coefficient is to use the rate of forward or reverse acceleration of the vehicle, as described in, for instance, Japanese Unexamined Patent Publication No. 60-99757. As is known from, for instance, Japanese Unexamined Patent Publication No. 4-328063, the road surface friction coefficient can be estimated based on a driving force applied to the driving wheels.

In regard to cases where the road surface friction coefficient is estimated based on acceleration of a vehicle in a direction of travel (which is referred in the specification to as longitudinal acceleration in contrast to lateral acceleration), there is no problem if the road surface is horizontal, but if the road surface changes from the horizontal plane, particularly if an uphill incline is encountered, the longitudinal acceleration decreases and thus causes a misreading of the road surface friction coefficient value toward the smaller side (which indicates that a traction loss is easily produced) with the result that the traction control impedes efficient acceleration and propulsion of the vehicle. On the other hand, in regard to cases where the road surface friction coefficient is estimated based on driving power transmitted to the driving wheels, when driving power transmission and road conditions are in balance, that is, when a driving condition is encountered in which the drive wheels run on the road without slippage, an accurate road surface friction coefficient can be estimated. When the driving power transmission and road conditions are not in balance, however, a relatively large error can be encountered in the estimation of road surface friction coefficient. In this instance where the road surface friction coefficient is calculated based on longitudinal acceleration, while it is possible to install a separate incline sensor in the system and to use the data output by the incline sensor to correct the estimated road surface friction coefficient. Incline sensors have been thought of as unnecessary and have generally not been employed in vehicles.

SUMMARY OF THE INVENTION

It is an object of the invention to provide a road surface condition determining system for application to an automotive vehicle which is capable of estimating an accurate road surface friction coefficient without the need for a road incline sensor.

The foregoing object is achieved by providing a road surface condition determining system for an automotive vehicle equipped with a traction control system which prevents driving wheels from encountering excessive relative rotation against a road or a vehicle or from losing traction of the driving wheels against a road surface.

The road surface condition determining system estimates, while the traction control is being executed, a first road surface friction coefficient on the basis of a vehicle speed and longitudinal acceleration in a straight-ahead travel direction and a second road surface friction coefficient on the basis of driving torque transmitted to the driving wheels, and determines an eventual road surface friction coefficient by selecting either one of the first and second road surface friction coefficients which is larger than the other for practical use in the traction control.

With the road surface condition determining system, because the larger one of the two road surface friction coefficients is selected as an eventual road surface friction coefficient the need for a road incline sensor is eliminated as well as the problem of the system estimating an eventual road surface friction coefficient as erroneously small. Even when loss of proper traction condition due to transmission of torque to the driving wheels in excess is encountered, that is, in a condition where there is a high possibility of causing significant error in the second road surface friction coefficient, an accurate road surface friction coefficient is established by preventing selection of the second road surface friction coefficient as the eventual road surface friction coefficient. Selection of the road surface friction coefficient as the active road surface friction coefficient is also prevented for a period of time from commencement of the traction control in which there is a high possibility of causing significant error in the second road surface friction coefficient, providing accurate estimation of the eventual road surface friction coefficient.

In the road surface condition determining system of the invention, a road surface friction coefficient estimated based on lateral acceleration of the vehicle may be utilized in order to effect an accurate estimation of the eventual road surface friction coefficient during a turning movement.

Accurate estimation of an eventual road surface friction coefficient is also enabled by subjecting the second road surface friction coefficient to filtering so as thereby to prevent it from changing abruptly. Further, accurate eventual road surface friction coefficient is estimated by establishing the second road surface friction coefficient in consideration of slippage of the torque converter which has a significant effect on torque transmission to the driving wheels. For accurate estimation of the eventual road surface friction coefficient, selection of the second road surface friction coefficient as the eventual road surface friction coefficient is prevented when the torque converter allows slippage in excess more than a specified amount, which bears a high possibility of erroneous estimation of the second road surface friction coefficient.

In the road surface condition determining system of the invention, a third road surface friction coefficient may be utilized and selected as the eventual road surface friction coefficient immediately after a vehicle start at which poor dependability is encountered in estimation of the second road surface friction coefficient due to a tendency for a large amount of torque to be applied in excess to the driving wheels, and also in estimation of the first road surface friction coefficient due to slow acceleration of the vehicle.

BRIEF DESCRIPTION OF THE DRAWINGS

The foregoing and other objects and features of the invention will be clearly understood from the following description with respect to an embodiment thereof when considered in conjunction with the accompanying drawings, in which:

FIG. 4 is an illustration showing a map of road surface friction value in relation to longitudinal acceleration;

FIG. 5 is an illustration showing a map of road surface friction value in relation to lateral acceleration;

FIG. 6 is an illustration showing a map of road surface friction value in relation to engine speed.

DETAILED DESCRIPTION OF THE EMBODIMENTS

Figure 1:
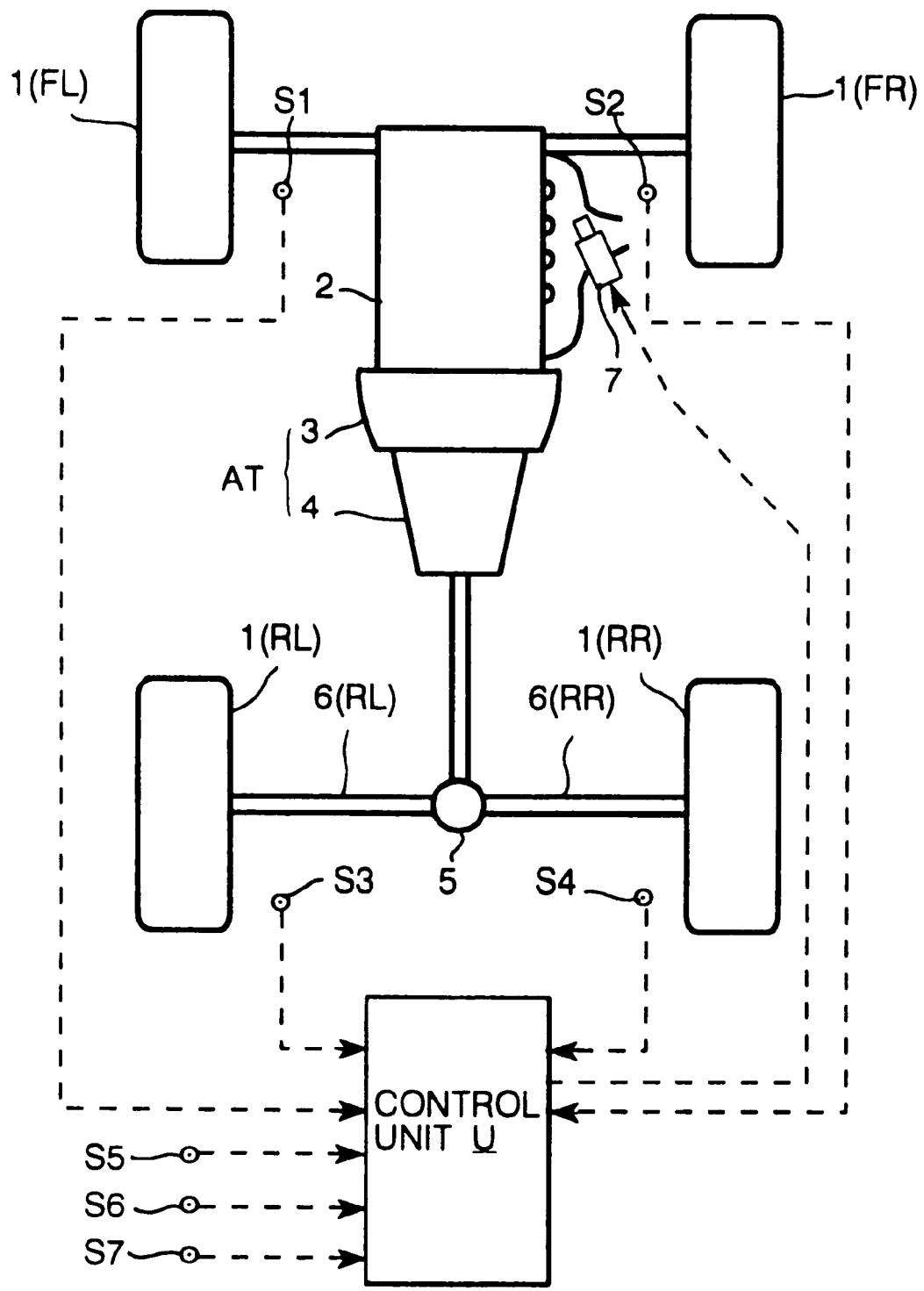
FIG. 1 is a schematic illustration of an automotive vehicle in which a road surface condition determining system of the invention is installed.

Referring to the drawings in detail, in particular, to FIG. 1 showing a vehicle 2, such as of a front engine rear drive type, equipped with a road surface condition monitoring system in accordance with an embodiment of the invention, the output torque from the engine 2 passes through an automatic transmission AT comprising a torque converter 3 and a transmission gear mechanism 4 after which it is applied to a differential gear set 5. The output torque is then transmitted from the differential gear set 5 to a left rear drive wheel 1(RL) through a left axle shaft 6(RL) and to a right rear drive wheel 1(RR) through a right axle shaft 6(RR). In this manner, the rear wheels 1(RL) and 1(RR) are forcibly rotated by the engine output power.

A control unit U, in which an integral microcomputer is incorporated, receives signals from various sensors S1–S7 and also outputs signals to a fuel injection valve 7. The speed sensors S1 through S4 are installed individually at each of the wheels and perform the function of independently monitoring the rotational speed of each wheel 1. The throttle sensor S5 monitors opening of the throttle valve (not shown), and the sensor S6 monitors the rotational speed of the engine 2. As will be stated later, it is necessary to monitor the speed of vehicle, therefore, in this embodiment, the speed sensors S1 and S2, mounted individually at front wheels 1(FL) and 1(FR), perform the function of monitoring vehicle speed by providing the individual speed signal from each front wheel 1 from which a geometric mean speed can be calculated. A separate vehicle speed sensor may be incorporated to provide a vehicle speed detection function.

Control unit U executes the traction control. This control is undertaken, for example, in the following manner. A slip value of rear driving wheels 1(RL) and 1(RR) against the road surface is calculated, for example, as the difference of the driving wheel speed from the vehicle speed. The greater this slip value is, the larger the amount of slippage of the driving wheels occurs against the pavement. A common slip value to the left and right rear driving wheels 1(RL) and 1(RR) is calculated as a geometric mean value of both slip values. Various types of threshold values are established based on the slip value; for example, a start-off control threshold value SS, a target slip value TE, and termination control threshold value ES, all of these threshold values being mutually related as the value TE is greater than the value ES but smaller than the value SS (SS>TE>ES).

If the common slip value to the left and right rear driving wheels 1(RL) and 1(RR) exceeds the start-off control threshold value SS, the traction control initiates by reducing the amount of fuel injected by the fuel injection valve 7 and thereby lowering torque generated by the engine 2 to a point where the common slip value approximates the target slip value TE in a feedback type of control. The extent of engine torque reduction increases as the deviation between the common slip value and target slip value TE increases. The traction control reduces the actual slip value and terminates when the actual slip value has become smaller than the target control value ES, or when the engine throttle is completely closed.

In regard the threshold values, as a minimum necessity, the target slip value TE is amended according to road surface friction coefficients (the relative friction coefficient between the road surface and the driving wheels). That is, the reduction of torque from the engine 2 increases as the road surface friction coefficient decreases, and it becomes difficult to ascertain the efficiency of acceleration if an erroneously small road surface friction coefficient is estimated.

The estimation of road surface friction coefficient executed will be described with reference to FIGS. 2 and 3 which show a flow chart illustrating the estimation sequence routine which the control unit U execute during the traction control.

When the sequence logic commences and control passes to the function block at step Q1 where various data are input. Subsequently, a longitudinal road surface friction coefficient $LG\mu$, which is referred to a road surface friction coefficient attribute to the longitudinal acceleration LGG and to simply as a longitudinal friction coefficient $LG\mu$, is estimated at step Q2, and a lateral road surface friction coefficient, which is referred to a road surface friction coefficient attribute to the lateral acceleration LTG and to simply as a lateral friction coefficient $LT\mu$, is estimated at step Q3. Further, a start-off road surface friction coefficient at a vehicle start, which is referred to simply as a start-off friction coefficient $ST\mu$, is estimated at step Q4, and a road surface friction coefficient attribute to propulsion force, that is, the torque applied to the driving wheels 1(RL) and 1(RR), which is referred to simply as a torque friction coefficient $TQ\mu$, is estimated at Q5. This propulsion force is obtained based on throttle opening and engine speed. Specifically, the propulsion force is a product of engine output torque multiplied by a gear ratio of a gear in use. A start of the vehicle is determined by, for instance, a means speed of the driven wheels attained a specified value. The engine output is mapped in relation to throttle opening TVO and engine speed Ne and stored in the control unit U. The in-use gear ratio is given on the basis of a signal from, for instance, a gear position sensor S7. At step Q6, one of these road surface friction coefficients $LG\mu$, $LT\mu$, $ST\mu$ and $TQ\mu$ is selected as an eventual road surface friction coefficient (which is referred to simply as an eventual friction coefficient) $\mu$ which in turn is utilized as a parameter from which the target slip value TE is varied in the traction control.

Figure 2:
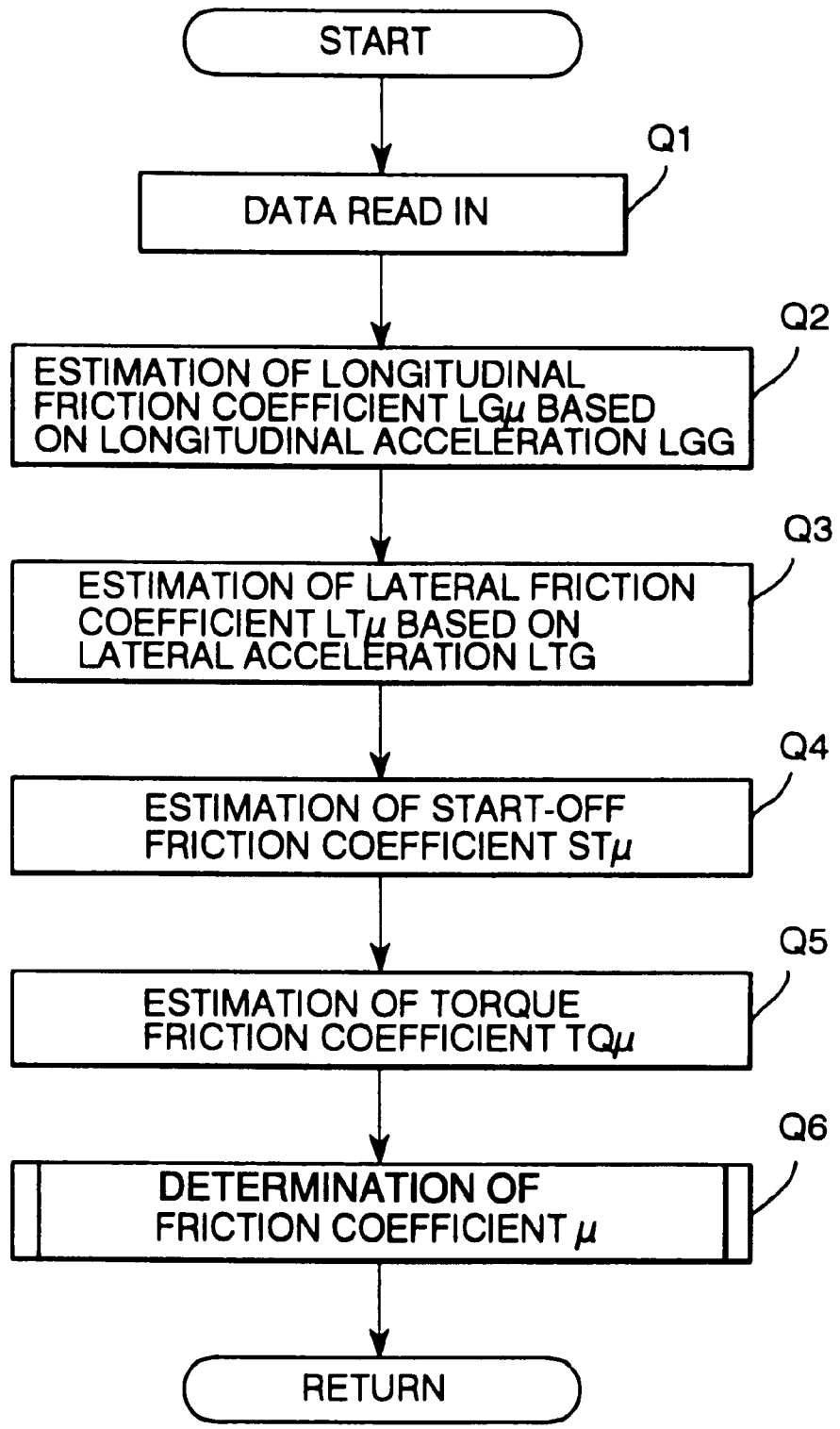
FIGS. 2 and 3 are flow charts illustrating a sequence routine of estimating a road surface friction coefficient.
Figure 3:
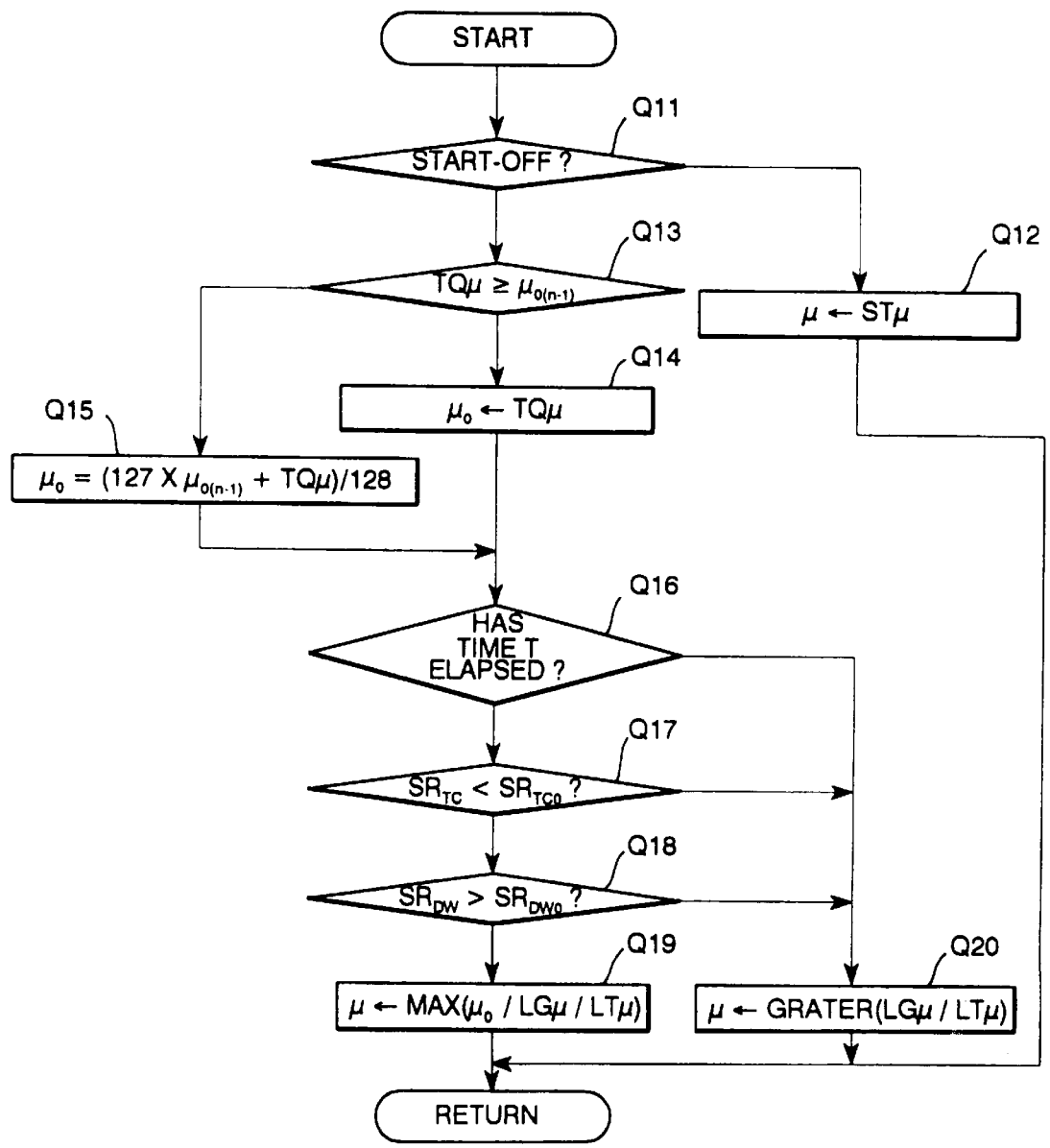

FIG. 3 shows the control sequence subroutine of determining or selecting the eventual friction coefficient $\mu$ executed at step Q6 of the road surface friction coefficient estimation routine in FIG. 2. The estimation of respective road surface friction coefficients $LG\mu$, $LT\mu$, $ST\mu$ and $TQ\mu$ made at steps Q2 through Q5, respectively, in the road surface friction coefficient estimation routine will be discussed later.

In the eventual friction coefficient $\mu$ determination subroutine, the first step at step Q11 is to make a determination as to whether the vehicle is in a start-from-stop state.

If in fact the vehicle is in a start-from-stop state, that is, if the answer to the determination is "YES," then, the control proceeds to step Q12 where the start-off friction coefficient STμ is selected as an eventual friction coefficient μ. On the other hand, if the answer to the determination made at step Q11 is "NO," filtering is applied to the friction coefficient μ through steps Q13 to step Q14. Specifically, a determination is made at step Q13 as to whether the current torque friction coefficient TQμ, which is an instantaneous value, is greater than the preceding eventual friction coefficient $\mu_{(n-1)}$ having been determined in a preceding cycle of the sequence routine. If the determination at Q13 results in a "NO" answer, this indicates that the torque friction coefficient TQμ must not be increasingly changed, then, the current torque friction coefficient TQμ is employed as a friction coefficient $\mu_{(n)}$ at step Q14. If the answer to the determination made at step Q13 is "YES," the torque friction coefficient TQμ is applied to the smoothing at step Q15 through which the current friction coefficient $\mu_{(n)}$ is calculated by the utilization of the following formula:

$$\mu_{(n)} = (127 \times \mu_{(n-1)} + TQ\mu)/128$$

As apparent in this formula, the current friction coefficient $\mu_{(n)}$ is given as a compound value of the preceding eventual friction coefficient $\mu_{(n-1)}$ and current torque friction coefficient TQμ at a predetermined relative proportion of, for instance in this embodiment, 127:1. In other words, part of 1/128 of the current torque friction coefficient TQμ is reflected on the friction coefficient $\mu_{(n)}$.

After the completion of establishing the current friction coefficient $\mu_{(n)}$, at step Q14 or at step Q15, a determination is made at step Q16 as to whether a specified period of time T has elapsed after commencement of the traction control. This specified time period has been established and denotes an expected time interval necessary for slippage of the driving wheels to disappear and, as a practical application, is determined as a constant time interval. If a "YES" answer is given in the determination at step Q16, a determination is further made at step Q17 as to whether a slipping rate $SR_{TC}$ of the torque converter 3 is less than a specified slipping rate $SR_{TCO}$, for example, 20%. The slipping rate is obtained from the following formula:

$$SR_{TC} = (Ne \times G1)/(Nw \times G2)$$

where

Ne is the engine speed;

G1 is the in-use gear ratio of the transmission;

Nw is the mean speed of driving wheels; and

G2 is the gear ratio of the differential.

If the answer to the determination is "YES," the a final determination is made at step Q18 as to whether the actual slipping rate $SR_{DW}$ of the driving wheels is below a specified slipping rate $SR_{DWO}$. This specified slipping rate $SR_{DWO}$ may be established, for example, as a value less than the start-off control threshold value SS and larger than the target slip value TE by a specific proportion.

If the answer to the decision made concerning the actual slipping rate $SR_{DW}$ made at step Q18 is "YES," this indicates that the torque friction coefficient TQμ attributes to the torque applied to the driving wheels, in particular the current friction coefficient $\mu_{(n)}$ amended based on the torque friction coefficient TQμ, is highly dependable, then, the largest friction coefficient is selected as an eventual friction coefficient μ among the longitudinal friction coefficient LGμ, lateral friction coefficient LTμ, and current friction coefficient $\mu_{(n)}$ at step Q19. On the other hand, if the answer to the determination concerning the time lapse made at step Q16 is no, if the answer to the determination concerning the slipping rate $SR_{TC}$ of the torque converter 3 made at step is "NO," or if the answer to the determination concerning the actual slipping rate $SR_{DW}$ of the driving wheels made at step Q18 is "YES," this indicates that the torque friction coefficient TQμ having been estimated based on the torque applied to the driving wheels, and hence the current friction coefficient $\mu_{(n)}$, is less dependable, then, either one of the longitudinal friction coefficient LGμ and lateral friction coefficient LTμ which is larger than the other is selected as an eventual friction coefficient μ at step Q19.

The following discussion concerns the manner of estimating the respective road surface friction coefficients LGμ, LTμ, STμ and TQμ made at steps Q2 through Q5 of FIG. 2, respectively. The road surface friction coefficient is rated as a value from "1" through "5" in which the value "1" denotes the lowest road surface friction coefficient representing a road surface offering minimal friction, such as an ice covered road, and in which the value "5" denotes the highest road surface friction coefficient representing a paved dry road surface.

FIG. 4 illustrates a map incorporated into the control unit U from which the longitudinal friction coefficient LGμ is rated in relation to longitudinal acceleration LGG and vehicle speed Nv as parameters. Under a constant vehicle speed, the longitudinal friction coefficient LGμ is rated at a higher value as the longitudinal acceleration LGG increases. Furthermore, the longitudinal friction coefficient LGμ is rated at a higher value as vehicle speed increases as long as the longitudinal acceleration LGG is constant. Accordingly, the longitudinal friction coefficient LGμ is obtained by means of comparing longitudinal acceleration LGG and vehicle speed Nv with those mapped as shown in FIG. 4. The vehicle speed Nv is obtained as a geometric mean value calculated from rotational speeds of the left front driven wheel 1(FL) and right front driven wheel 1(RL) as monitored by the speed sensors S1 and S2, respectively. The longitudinal acceleration is obtained through a differential calculation of the vehicle speed. The lateral acceleration may be calculated on the basis of the difference between driven wheel speeds, or otherwise detected by an extra lateral acceleration sensor.

FIG. 5 illustrates a map incorporated into the control unit U from which a lateral friction coefficient LTμ is rated in accordance with lateral acceleration LTG as a parameter. As shown in FIG. 5, the lateral friction coefficient LTμ is rated at a higher value as the lateral acceleration LTG increases. Accordingly, the lateral friction coefficient LTμ is rated by means of comparison of an actual lateral acceleration LTG with those in the map shown in FIG. 5. While the lateral acceleration LTG may be obtained through a dedicated acceleration sensor installed specifically for detecting lateral acceleration LTG, this embodiment presented here obtains lateral acceleration LTG based on the rotational difference between the left and right driven wheels. The start-off road surface friction coefficient STμ is estimated as a value based on engine rotational speed when a specific and relatively large amount of slippage is generated at the driving wheels. A map shown in FIG. 6 is incorporated into the control unit U and is used to rate start-off friction coefficient STμ according to engine speed Nv. The map shown in FIG. 6 map is provided for specific transmission speeds, for example in this embodiment a first gear and a second gear.

Torque friction coefficient TQμ is obtained from the following formula:

$$TQ\mu=(A\times T\times G1\times G2\div R\div W)\times K$$

wherein

T is the engine output torque;

G1 is the in-use gear ratio of the transmission 4;

G2 is the gear ratio of the differential gear 5;

R is the radius of each driven wheel 1(RL), 1(RR);

W is the vehicle weight;

K is the transformation factor of road surface friction coefficient; and

A is the constant.

The value included in parentheses corresponds to the theoretical longitudinal acceleration for the vehicle. The transformation factor K alters the theoretical longitudinal acceleration into a road surface friction coefficient $\mu$ and is, as a practical example established as 5/0.55. That is, the torque friction coefficient $TQ\mu$ is formulated such that, it takes a value of "5" when the theoretical longitudinal acceleration is at 0.55 and that it is limited to the largest value of "5".

Torque T generated by the engine 2 is mapped in relation to throttle opening TVO and engine speed Ne. The throttle opening compared with that in the torque map is either one of a physical throttle opening monitored by the throttle sensor S5 and a theoretical throttle opening obtained on the basis of current engine operating conditions, including the amount of fuel injection, an ignition timing and other engine control parameters, which is smaller than the other.

Figure 7:
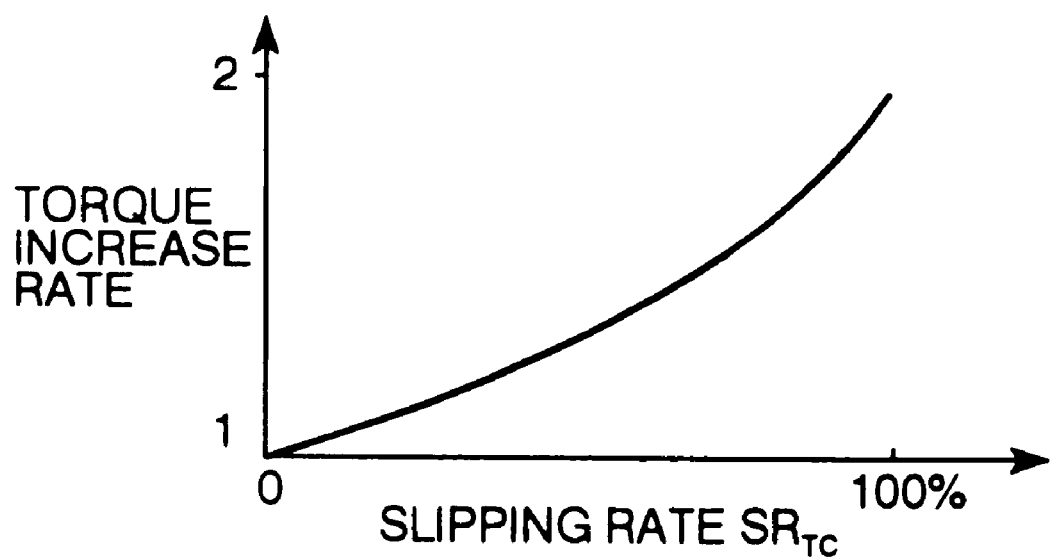
FIG. 7 is a diagrammatic illustration showing a map of slipping rate of a torque converter in relation to torque increasing ratio.

The relationship between the slip rate and torque increase rate of the torque converter 3 is shown in FIG. 7 and is incorporated as a torque converter slip rate map into the control unit U. Even in cases where there is a large slip rate in the torque converter 3, it is enabled to estimate an road surface friction coefficient utilizing the torque friction coefficient $TQ\mu$ by applying the torque increase rate to the previously mentioned torque friction coefficient calculation formula. Incorporating the torque converter slip rate map into the control unit U can eliminate the procedure or determination taken at step Q17 in the sequence subroutine of determining the eventual friction coefficient $\mu$ shown in FIG. 3.

Although the invention has been described by way of example in relation to specific embodiments, it is to be understood that the invention is not limited to the embodiments described above, but can also be embodied as delineated in the following discussion.

An adequate ratio may be derived as a "slip rate" of the driving wheels against a road surface rather than the "speed difference" between the speed of driving wheels and vehicle speed like a dummy vehicle speed. For example, the slip rate may be represented by a ratio of the speed of driving wheel relative to the speed of vehicle or by a ratio of the speed difference" between the speed of driving wheels and vehicle speed relative to the speed of vehicle. The estimated road surface friction coefficient (eventual road surface friction coefficient) may be effectively applied to antilock barking control as well as the traction control.

The start-off road surface friction coefficient may be utilized even when the traction control is not executed. In conjunction with or in place of reducing engine output torque in order to effect the traction control, an engine ignition timing may be retarded. Alternatively, a secondary throttle valve may be installed as the means by which engine output torque is reduced.

The traction control may be performed by braking the driving wheels in place of or in conjunction with lowering engine output torque. In such braking force control is employed, the braking force applied to the driving wheels may be applied through adjusting the pressure of hydraulic fluid in the braking system, and the reduction in engine output torque effected through the application of the braking force.

It is to be understood that although the present invention has been described with regard to preferred embodiments thereof, various other embodiments and variants may occur to those skilled in the art, which are within the scope and spirit of the invention, and such other embodiments and variants are intended to be covered by the following claims.

What is claimed is:

1. A road surface condition determining system for an automotive vehicle equipped with a traction control feature which provides prevention of relative rotation in excess of driving wheels against a road for determining an eventual road surface friction coefficient which is used in traction control, said road surface condition determining system comprising:

speed detecting means for detecting a speed of the vehicle;

a torque sensor for detecting engine output torque and a selected transmission gear and for determining driving torque transmitted to the driving wheels based on said engine output torque and said selected transmission gear; and road surface friction coefficient determining means for detecting longitudinal acceleration of the vehicle in a straight-ahead travel direction from a vehicle speed detected by said speed detecting means, for estimating, while traction control is being executed, a first road surface friction coefficient on the basis of said vehicle speed and said longitudinal acceleration and a second road surface friction coefficient on the basis of driving torque detected by said torque sensor, for determining either one of said first and second road surface friction coefficients which is larger than the other as an eventual road surface friction coefficient and for inhibiting determination of said second road surface friction coefficient as said eventual road surface friction coefficient for a predetermined period of time after commencement of said traction control.

2. A road surface condition determining system as defined in claim 1, wherein said speed detecting means comprises speed sensors for detecting wheel speeds of driven wheels of the vehicle, respectively, and said road surface friction coefficient determining means calculates a mean of said driven wheel speeds as said vehicle speed.

3. A road surface condition determining system as defined in claim 1, wherein said speed detecting means comprises speed sensors for detecting driving wheel speeds of driving wheels of the vehicle, respectively, and said road surface friction coefficient determining means calculates a slipping rate on the basis of said vehicle speed and said driving wheel speed.

4. A road surface condition determining system as defined in claim 3, wherein said road surface friction coefficient determining means inhibits determination of said second road surface friction coefficient as said eventual road surface friction coefficient when said slipping rate is greater than a specified rate.

5. A road surface condition determining system as defined in claim 1, wherein said road surface friction coefficient determining means includes filtering means for varying said second road surface friction coefficient in a specified relationship.

6. A road surface condition determining system as defined in claim 1, wherein said road surface friction coefficient determining means further detects lateral acceleration of the vehicle during cornering from a vehicle speed detected by said speed detecting means, estimating, while traction control is being executed, estimates a third road surface friction coefficient on the basis of said lateral acceleration, and determines the largest one of said first, said second and said third road surface friction coefficients as an eventual road surface friction coefficient.

7. A road surface condition determining system as defined in claim 6, wherein said road surface friction coefficient determining means determines said lateral acceleration based on said driven wheel speeds.

8. A road surface condition determining system as defined in claim 7, and further comprising an engine speed detecting means for detecting a rotational speed of an engine, wherein said road surface friction coefficient determining means estimates a fourth road surface friction coefficient on the basis of said engine speed when a slipping rate of the driving wheels against a road reaches a specified rate and selects said fourth road surface friction coefficient, as an eventual road surface friction coefficient, prior to said first to third road surface friction coefficients.

9. A road surface condition determining system, for an automotive vehicle having an automatic transmission equipped with a torque converter, for determining an eventual road surface friction coefficient which is used in traction control which provides prevention of relative rotation in excess of driving wheels against a road, said road surface condition determining system comprising:

speed detecting means for detecting a speed of the vehicle;

a torque sensor for detecting engine output torque and a selected transmission gear and for determining driving torque transmitted to the driving wheels based on said engine output torque and said selected transmission gear;

slip detecting means for detecting slipping rate of the torque converter; and road surface friction coefficient determining means for detecting longitudinal acceleration of the vehicle in a straight-ahead travel direction from a vehicle speed detected by said speed detecting means, for estimating, while traction control is being executed, a first road surface friction coefficient on the basis of said vehicle speed and said longitudinal acceleration and a second road surface friction coefficient on the basis of driving torque detected by said torque sensor, for correcting said second road surface friction coefficient with said slipping rate, for determining either one of said first road surface friction coefficients and said second road surface friction coefficient after correction which is larger than the other as an eventual road surface friction coefficient and for inhibiting determination of said second road surface friction coefficient as said eventual road surface friction coefficient for a predetermined period of time after commencement of said traction control.

10. A road surface condition determining system as defined in claim 9, wherein said road surface friction coefficient determining means inhibits determination of said second road surface friction coefficient after correction as said eventual road surface friction coefficient when said slipping rate is greater than a specified rate.

11. A road surface condition determining system as defined in claim 9, further comprising an engine speed detecting means for detecting a rotational speed of an engine, wherein said road surface friction coefficient determining means estimates a third road surface friction coefficient on the basis of said engine speed when a slipping rate of the driving wheels against a road reaches a specified rate and selects said third road surface friction coefficient, as an eventual road surface friction coefficient, prior to said first and second road surface friction coefficients.

12. A road surface condition determining system as defined in claim 9, wherein said road surface friction coefficient determining means inhibits determination of said second road surface friction coefficient as said eventual road surface friction coefficient when said slipping rate is greater than a specified rate.

13. A road surface condition determining system as defined in claim 9, wherein said road surface friction coefficient determining means further detects lateral acceleration of the vehicle during cornering from a vehicle speed detected by said speed detecting means, estimating, while traction control is being executed, estimates a third road surface friction coefficient on the basis of said lateral acceleration, and determines the largest one of said first, said second and said third road surface friction coefficients as an eventual road surface friction coefficient.

14. A road surface condition determining system as defined in claim 13, wherein said road surface friction coefficient determines said lateral acceleration based on said driven wheel speeds.

15. A road surface condition determining system as defined in claim 14, and further comprising an engine speed detecting means for detecting a rotational speed of an engine, wherein said road surface friction coefficient determining means estimates a fourth road surface friction coefficient on the basis of said engine speed when a slipping rate of the driving wheels against a road reaches a specified rate and selects said fourth road surface friction coefficient, as an eventual road surface friction coefficient, prior to said first to third road surface friction coefficients.

\* \* \* \* \*